Figure 1:
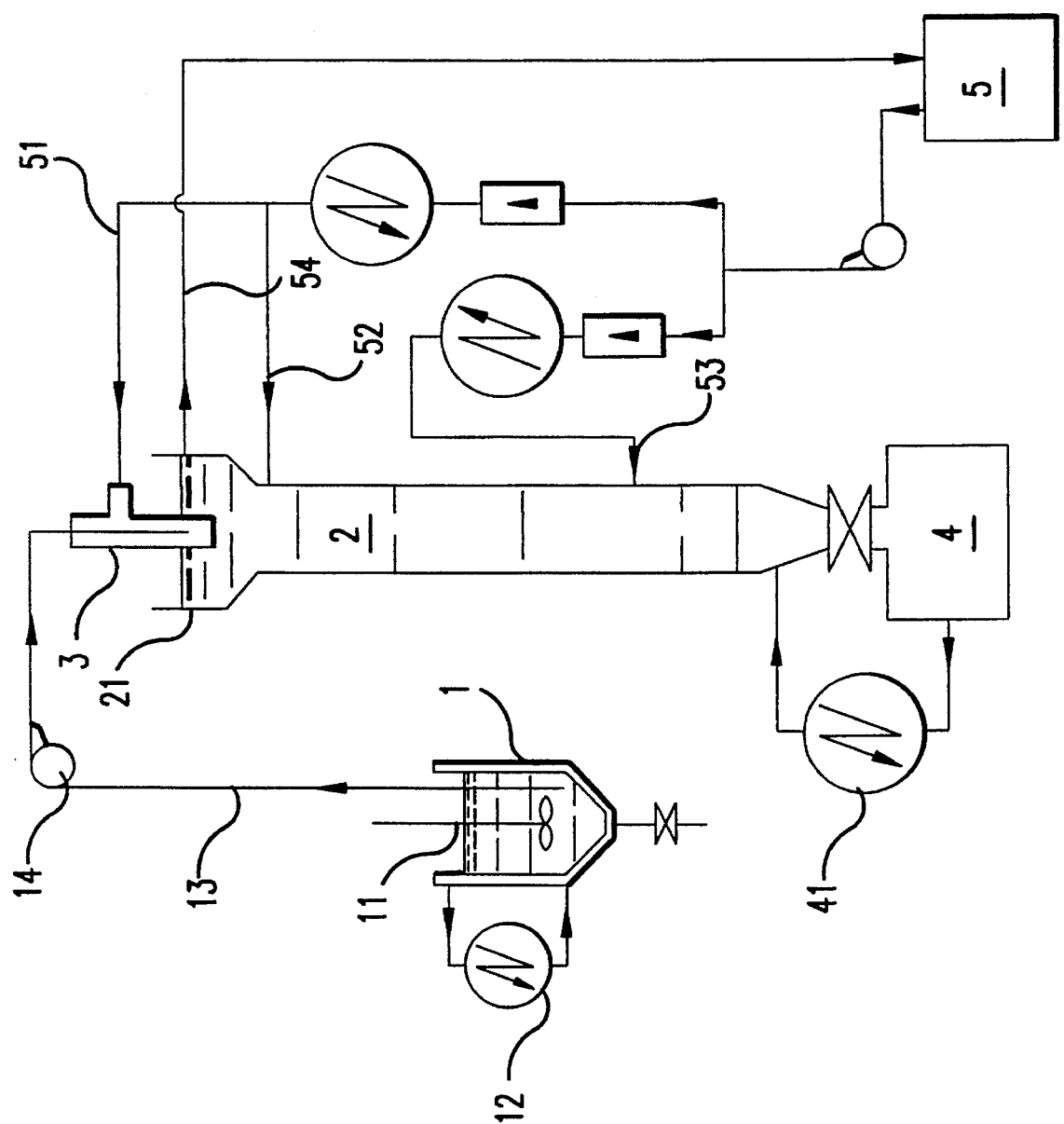

United States Patent [19]

Cheminal et al.

[11] Patent Number: 5,523,500
[45] Date of Patent: Jun. 4, 1996

[54] MASS CATALYSTS BASED ON CHROMIUM AND NICKEL OXIDES AND THEIR APPLICATION TO THE FLUORINATION OF HALOGENATED HYDROCARBONS

[75] Inventors: Bernard Cheminal, Brignais; Francois Garcia, Saint Genis Laval; Eric Lacroix, Lyons; Andre Lantz, Vernaison, all of France

[73] Assignee: d'Elf Atochem S.A., Puteaux, France

[21] Appl. No.: 387,979

[22] Filed: Feb. 13, 1995

Related U.S. Application Data

[63] Continuation of Ser. No. 968,394, Dec. 7, 1992, abandoned.

[30] Foreign Application Priority Data

Dec. 9, 1991 [FR] France .................... 91 15228

[51] Int. Cl.$^6$ .................. C07C 17/087; C07C 17/07; B01J 23/86; B01J 23/755
[52] U.S. Cl. .................. 570/169; 502/315; 502/257; 502/314; 502/8
[58] Field of Search .................. 502/315, 257, 502/314, 8; 570/169

[56] References Cited

U.S. PATENT DOCUMENTS

| | | | |
|---|---|---|---|
| 2,435,551 | 2/1948 | Black | 502/315 X |
| 2,900,423 | 8/1959 | Smith | 502/315 X |
| 3,661,805 | 5/1972 | Horvath | 502/315 |
| 3,804,778 | 4/1974 | Ramanadin | 502/228 |
| 4,131,616 | 12/1978 | Stiles | 518/706 |
| 4,439,534 | 3/1984 | Foulletier | 502/256 X |
| 4,912,270 | 3/1990 | Carlson et al. | 570/169 |
| 5,185,482 | 2/1993 | Manzer | 570/168 |
| 5,354,928 | 10/1994 | Cheminal et al. | 570/169 |

FOREIGN PATENT DOCUMENTS

| | | |
|---|---|---|
| 0055652 | 7/1982 | European Pat. Off. . |
| 0128510 | 12/1984 | European Pat. Off. . |
| 486333 | 5/1992 | European Pat. Off. . |
| 2276098 | 1/1976 | France . |
| 2407021 | 5/1979 | France . |
| 2-178237 | 7/1990 | Japan ..................... 502/315 |

*Primary Examiner*—Douglas J. McGinty
*Attorney, Agent, or Firm*—Spencer & Frank

[57] ABSTRACT

The invention relates to mass catalysts based on chromium and nickel oxides, obtained from a sol of chromium and nickel hydroxides.

These catalysts, in which the Ni/Cr atomic ratio is between 0.05 and 5, may be used from the fluorination of halogenated hydrocarbons by HF in the gas phase.

17 Claims, 2 Drawing Sheets

MASS CATALYSTS BASED ON CHROMIUM AND NICKEL OXIDES AND THEIR APPLICATION TO THE FLUORINATION OF HALOGENATED HYDROCARBONS

This is a continuation of application Ser. No. 07/986,394, filed on Dec. 7, 1992, now abandoned.

FIELD OF THE INVENTION

The present invention relates to the fluorination of halogenated hydrocarbons by gas phase catalysis and more particularly relates to new mass catalysts based on chromium and nickel and their application to the synthesis of hydrohaloalkanes.

BACKGROUND OF THE INVENTION

The intensive research currently conducted on substitutes for chlorofluorocarbons (CFCs) is directed, inter alia, towards the synthesis of hydrohaloalkanes. Some steps of this synthesis may be carried out by fluorination with hydrofluoric acid by heterogeneous gas phase catalysis.

Very numerous metal compounds (for example chromium, cobalt, nickel, iron, copper, manganese, and the like) have a catalytic effect for these fluorination reactions. The catalysts proposed in the literature are either mass catalysts or supported catalysts, the support being mainly carbon or alumina (partially convened to $AlF_3$ after fluorination).

Amongst this second category, a large variety of metal compounds are found and there are numerous patents describing fluorination processes based on this type of catalyst. Thus, mention may be made of the patents U.S. Pat. Nos. 2,744,147 and 2,744,148, which describe the fluorination of a haloalkane on a catalyst based on a metal (chromium, cobalt or nickel for the patent U.S. Pat. No. 2,744,147 and chromium, cobalt, nickel, copper or palladium for the patent U.S. Pat. No. 2,744,148) supported on alumina.

More recently, the patent EP 0 366 797 describes a fluorination process using a catalyst consisting of at least one metal (nickel, cobalt, iron, manganese, chromium, copper and silver) fluoride supported on an alumina having a significant mesoporosity.

For all of these catalysts, the support imparts a certain solidity to them. However, as the amount of active material is smaller than in a mass catalyst, the catalytic activity may be affected. Moreover, these low contents of non-precious metals do not enable their recovery from spent catalysts to be envisaged in an economic manner.

The mass fluorination catalysts are mainly based on chromium and the starting materials used for their development are very varied (salts, oxides, halides and the like).

Thus, the patents U.S. Pat. No. 4,912,270 and EP 0 313 061 claim fluorination processes using catalysts based on chromium oxide which are obtained, respectively, by reduction of chromium trioxide by means of an alcohol and by pyrolysis of ammonium bichromate.

The patent FR 2 135 473 describes the preparation of a catalyst containing chromium and nickel and its use in the fluorination of functional perhalogenated compounds. This catalyst is obtained by thermal decomposition of organic chromium and nickel salts. The nickel contents remain low since the Ni/Ni+Cr atomic ratio is still less than 0.1.

The patent publications JP 2-172932/90 and 2-172933/90 describe, respectively, the fluorination of 1,1-difluoro-1,2,2-trichloroethane (F122) and of 1-chloro-2,2,2-trifluoroethane (F133a) on a chromium catalyst to which a doping metal has been added which enables the reaction temperature to be lowered while maintaining a significant activity and therefore improves the life of the catalyst by restricting the crystallization of the chromium. The chromium/nickel combination is not illustrated by the examples in these publications.

The patent FR 2 501 062 describes the preparation of a mass chromium oxide in the form of microspheres having a diameter of between 0.1 and 3 mm. This catalyst is obtained by gelling a chromium hydroxide sol in a solvent which is immiscible or partially miscible with water. The product obtained is highly solid and is particularly suitable for fluorination reactions in a fluidized bed.

The disadvantage of catalysts based on chromium oxide is their low resistance at high temperature (350°–500° C.) to the crystallization which contributes to reducing their life.

Moreover, these chromium-based catalysts promote the oxidation of hydrochloric acid by the oxygen dissolved in the reagents or deliberately introduced. Water and chlorine form by a Deacon reaction (Chemical Week 1987, 24 Jun., page 18) and these in turn react with the organic compounds, which leads to the formation of non-valorizable by-products and, consequently, to a lowering of the selectivities.

It has now been found that the addition of a nickel compound to a chromium derivative in order to form a sol of chromium and nickel hydroxides makes it possible, while retaining the advantages of a mass catalyst, not only to prolong the life of the catalyst by improving the resistance of the chromium-based compound to crystallization but also to improve the selectivities in gas phase fluorination reactions owing to a partial inhibition of the oxidation of hydrochloric acid in the presence of chromium.

DESCRIPTION OF THE INVENTION

The invention therefore relates to mass catalysts based on chromium and nickel oxides, obtained by a process essentially consisting in:

a) forming a sol of chromium(III) and nickel(II) hydroxides,
b) gelling this sol, and
c) drying and calcining the product to a temperature of between 250° and 450° C.

The invention also relates to the application of these catalysts to the fluorination of saturated or olefinic halogenated hydrocarbons by HF in the gas phase.

In the catalysts according to the invention, which may be in various forms (spheres, extruded products, pellets, and the like ) the Ni/Cr atomic ratio may range from 0.05 to 5. It is advantageously between 0.1 and 3.5 and preferably between 0.15 and 3.

Depending on the gelling technique used (in form of droplets or in mass), the catalyst precursor, consisting of a homogeneous mixture of chromium and nickel hydroxides, is obtained, which, after drying, is either in the form of microspheres or in the form of a powder which may be shaped using well-known techniques, for example by extrusion or by pelleting. After calcination, a mass catalyst consisting of a homogeneous mixture of chromium and nickel oxides is obtained.

The sol of chromium(III) and nickel (II) hydroxides may be formed in a manner known per se from chromium and nickel precursors.

Chromium precursors which may be mentioned are chromium, oxides, hydroxides, halides, oxyhalides, acetates, nitrates and sulphates, but it is also possible to use any other chromium compound capable of leading to a chromium hydroxide sol. The preferred precursors are chromium salts such as the sulphates, chlorides, acetates and nitrates, the chromium(III) sulphate or acetate being more particularly preferred.

Nickel precursors which may be mentioned are the hydroxides, oxyhalides, nitrate, acetate and sulphates of this metal, but it is also possible to use any other nickel compound which is soluble in water and capable of forming a sol or of being incorporated in the chromium gel. The preferred precursors are the highly soluble salts, such as nickel nitrates and especially nickel chlorides or sulphates.

With certain precursors of chromium and nickel, particularly the oxides, hydroxides, acetates and sulphates, the sol may be formed at room temperature. On the contrary, where the precursor is a chromium nitrate or halide, the formation of the sol needs a heating step at a temperature comprised between 60° and 100° C., preferably between 80° and 95° C. Furthermore, even when the nature of the precursor permits the sol to be formed at low temperature, it is advantageous to heat the solution of precursors at a temperature of between 60° and 100° C., preferably between 80° and 95° C.

The formation of the sol may also be improved by adding to the aqueous solution of the precursors a complexing agent for chromium and/or nickel such as, for example, ammonium acetate, sulphate or phosphate, in a molar amount which may go up to five times the total number of moles of the chromium and nickel precursors.

Diverse additives may be added to the sol in order to perfect the physicochemical and catalytic properties of the final catalyst. Thus, it is possible to add (% relative to the weight of the sol):

a) 2 to 10% of $Cr_2O_3$ or $Cr_2O_3.2H_2O$ powder previously dried at 300° C. in order to increase the mechanical strength of the microspheres;

b) 0.1 to 3% of alumina monohydrate in order to increase the resistance to attrition of the catalyst;

c) 5 to 25% of hexamethylenetetramine and/or urea, the presence of which leads, by decomposition at the gel temperature of the sol, to an additional evolution of ammonia;

d) 1 to 10% of colloidal silica in order to increase the porosity of the catalyst (the silica is removed in the form of silicon tetrafluoride during the treatment with hydrofluoric acid);

e) other additives, such as wetting agents (for example lauryldiethanolamide or polyethylene glycol monostearate) or thickeners (for example hydroxymethylcellulose or microcrystalline cellulose) in order to improve the spherical nature of the microspheres.

Using the sol of chromium and nickel hydroxides as the starting material, the mixed chromium and nickel oxide catalysts according to the invention may be obtained in the form of microspheres by gelling the sol in the following way:

1) dispersing the sol in the form of droplets in an organic solvent which is immiscible or sparingly miscible with water and gelling at elevated temperature;

2) receiving the microspheres formed in the gelling solvent or in an ammonia solution in order to complete gelling;

3) washing the micropheres with dilute ammonia and with water in order to remove the impurities, and optionally drying.

First Step

The formation and the gelling of the microspheres are carried out in a column having a height of between 1 and 6 m, which column is extended by a release zone and has a stream of hot solvent passing through it from bottom to top.

The sol of chromium and nickel hydroxides is injected at the top of the column by means of a tube of small diameter arranged concentrically inside another tube of larger diameter, through which the solvent cooled to a temperature not exceeding 30° C. (preferably 25° C.) arrives in co-current in order to prevent gelling in the injectors.

The diameter of the injector and the flow of the sol determine the dispersion of the droplets and consequently the final size of the microspheres. During its injection, it is expedient to keep the sol at a temperature of between 2° and 8° C., preferably between 3° and 5° C., so as to prevent variations in its viscosity. These variations are reflected in a change in the sol and, consequently, in the physicochemical properties of the microspheres.

It is advantageous to partially neutralize the sol, before its injection, with an amount of ammonium hydroxide sufficient to obtain a viscosity adapted to the dispersion of the droplets. This amount depends on the nature of the chromium and nickel precursors used. The $NH_4OH/Cr+Ni$ molar ratio is advantageously less than 2 and preferably less than 1.5.

The ascending stream of hot solvent (temperature of between 25° and 140° C.) is introduced at the base of the column at an ascending speed of between 0.1 and 5 m/s. This speed determines the residence time of the microspheres and, consequently, their degree of gelling.

In its upper part, the column may be provided with a second inlet for solvent cooled to a temperature not exceeding 30° C. This facilitates the maintenance of a temperature gradient in the column and enables the gelling rate to be controlled.

The organic solvent which is immiscible or sparingly miscible with water may be chosen from alcohols, such as butanol, hexanol, 2-ethylpentanol and 2-ethylhexanol, this latter alcohol being particularly preferred.

Second Step

On leaving the bottom of the column, the microspheres are collected in a vessel containing the organic gelling solvent or, preferably, containing aqueous ammonia, the concentration of which may be between 0.1 and 14N and the temperature of which is kept between 15° and 70° C., preferably between 25° and 50° C.

The presence of ammonia in the vessel effectively completes the gelling of the microspheres, thus increasing their mechanical strength and also ensuring the first washing. An increase in the concentration of the ammonia solution enables the solidity and the density of the microspheres to be increased.

Third Step

The microspheres are washed several times with dilute ammonia (0.1 to 1N) and then with water, before optionally being dried in air at a temperature of between 80° and 200° C. However, this drying at low temperature may be omitted without risk of altering the properties of the microspheres.

The microspheres are then calcined under inert gas (for example nitrogen, argon or the like) or in air at a temperature of between 250° and 450° C., preferably between 300° and 420° C.

Instead of being gelled in the form of microspheres in accordance with the method described above, the sol of chromium and nickel hydroxides may be completely gelled by adding a base, preferably aqueous ammonia, until the sol of hydroxides solidify. The product obtained is then washed with dilute ammonia (0.1 to 1N) and/or with water, before being dried at a temperature of between 80° and 200° C. The washings and filtrations may be made easier by adding from 5 to 100 ppm of a flocculant, preferably a polyacrylamide. The catalyst is then calcined in the same manner as described above, this calcination being able to be preceded or followed by a shaping step using known techniques (extrusion, pelleting).

The mass catalysts according to the invention may be used for the fluorination of saturated or olefinic halogenareal hydrocarbons by HF in the gas phase. They are particularly suitable for the fluorination of halogenated hydrocarbons leading to fluorinated $C_1$ to $C_3$ compounds containing one or more hydrogen atoms. The following compounds may be mentioned, without any limitation being implied, as examples of starting halogenated hydrocarbons: $CHCl_3$, $CCl_2=CHCl$, $CHCl_2-CClF_2$, $CH_2Cl-CF_3$, $CH_3-CCl_2-CH_3$, $CCl_3-CF_2-CH_3$, $CCl_3-CF_2-CHCl_2$, $CCl_3-CF_2-CH_2Cl$, $CHCl_2-CHCl-CH_3$, $CH_2Cl-CHCl\leq CH_3$ and also $CCl_2=CCl_2$; this latter compound does not contain hydrogen, but the addition of HF leads to hydrohalogenated compounds.

In order to work at the optimum activity, the catalyst requires a treatment with hydrofluoric acid, which is undiluted or diluted with nitrogen. Although the presence of nickel slows down the crystallization of the catalyst, an activation of this type may locally generate temperatures higher than 500° C. it is for this reason that it is recommended to control the exothermicity of the activation by adjusting the addition of a diluent for HP and by starting this treatment at low temperature (150°–250° C.). On the other hand, after passing through "exothermicity waves" in the catalyst bed, it is advised that the temperature be progressively increased in order to reach a maximum of 350°–450° C. at the end of activation.

The fluorination reaction temperature depends on the reaction studied and, of course, on the desired reaction products. Thus, for a partial replacement of chlorine atoms by fluorine, the reaction is carried out at temperatures of between 50° and 350° C.; the replacement of all of the chlorine atoms may require temperatures of between 300° and 500° C.

The contact time also depends on the reaction studied and the desired products. In general it is between 3 and 100 seconds; however, in order to obtain a good comprise between high degree of conversion and high productivity, this contact time generally remains less than 30 seconds.

The HF/organic compound molar ratio is also linked to the reaction studied: it depends, inter alia, on the stoichiometry of the reaction. In the majority of cases it may vary between 1/1 and 20/1, but, in this case also, in order to obtain high productivities it is often less than 10.

The operating pressure is preferably between 1 and 20 bars absolute (0.1 to 2 MPa).

The catalysts according to the invention may operate in a fixed bed or in a fluidized bed. The catalysts in the form of microspheres are very solid and therefore particularly suitable for reactions in a fluidized bed.

Catalysts for which the activity has fallen as a consequence of contamination may be regenerated by cleaning the catalyst with a compound capable of oxidizing and converting the products (organic products, coke, and the like) deposited on the catalyst into volatile products. In this capacity, oxygen or a mixture containing oxygen (air for example) is perfectly suitable and enables the initial catalyst activity to be restored.

In order to ensure the regeneration of the catalyst without inducing crystallization it is recommended to carry out this treatment at a temperature of between 200° and 450° C. and more particularly between 300° and 380° C. Similarly, it is expedient to limit the exothermicity of this "combustion" by controlling the oxygen flow rate the start of regeneration, low flow rate of oxygen diluted in an inert gas) so as to maintain a temperature of below 450° C.

In order to maintain the activity of the catalyst, it is also possible to carry out the fluorination reaction in the presence of oxygen introduced in a $O_2$/organic compound molar ratio which can range from 0.001 to 0.05 and is preferably between 0.005 and 0.03.

EXAMPLES

The following examples illustrate the invention without restricting it. The pore volume in Examples 1 to 12 was determined by mercury porosimetry and corresponds to that of the pores having a radius comprised between 4 nm and 63 μm.

PREPARATION OF THE CATALYSTS

EXAMPLE 1

Catalyst A

The procedure is carried out in the apparatus which is shown in appended FIG. 1 and comprises the following main elements:

a glass reactor (1) which has a volume of 3 liters, for the preparation of the sol of chromium and nickel hydroxides; it is provided with a double wall and fitted with a biconical stirrer (11) rotating at 3000 rev/min; a pump and a heat exchanger (12) make it possible to remove the calories from the neutralization and thus to keep the sol at the desired temperature;

a glass column (2) for gelling the sol in the form of microspheres; this column (80 mm in diameter and 1.5 m high) is; extended at the top by a release zone (21) 100 mm in diameter and 100 mm high;

an injector device (3) consisting of a tube having an internal diameter of 2 mm for the injection of the sol into the column 2; this tube is arranged concentrically inside a tube having an internal diameter of 12 mm, through which 2-ethylhexanol is injected;

a receiving tank (4) for collecting the microspheres formed in the column 2; this tank, which has a volume of 5 liters, contains aqueous ammonia which is homogenized and kept at the desired temperature by means of a circuit comprising a pump and a heat exchanger (41);

a reservoir (5) for feeding the injector device 3 and the column 2 with 2-ethylhexanol serving as dehydrating solvent.

a) Preparation of the Sol of Chromium and Nickel Hydroxides

In aqueous chromium and nickel solution is prepared at room temperature by dissolving 550 g of basic chromium sulphate $Cr_2(SO_4)_2(OH)_2Na_2SO_4$ and 238 g of nickel chloride hexahydrate $NiCl_2.6H_2O$ in 367 g of water. 70 g of crystalline chromium(III) oxide are then added to this aqueous solution.

The mixture is cooled to 5° C. and, while maintaining this temperature, the following are added successively:

151.5 g of cold 11N ammonia (5° C.), a cold (5° C.) aqueous solution comprising 204 g of hexamethylenetetramine, 10.8 g of urea and 300 ml of water, and 225 g of a 30% silica sol in water (CECASOL from CECA).

b) Injection of the Sol and Synthesis of the Microspheres

The sol of chromium and nickel hydroxides, prepared in step a), is then routed towards column 2 through the line (13) by means of a pump (14). The use of a peristaltic pump enables any variation in flow rate to be avoided. For significant lengths of routing line 13, it is necessary to sheath the line in order to prevent refrigerating losses.

The sol at 5° C. is injected at a rate of 0.6 l/h through the tube having an internal diameter of 2 mm, while 2-ethylhexanol at a temperature of 25° C. is injected through the line 51 at a flow rate of 10 l/h by means of the tube having am internal diameter of 12 mm in order to prevent premature gelling of the sol in the injector device 3; the end of the latter is immersed about 5 mm into the organic solvent. A flow of 2-ethylhexanol at the same temperature (25° C.) may be passed into the upper part of the column through a line 52, the inlet of which is located below the release zone.

Another stream of 2-ethylhexanol, heated to a temperature of 120° C., is introduced at a flow rate of 45 l/h into the bottom of the column through the line 53. This stream of 2-ethylhexanol passes through the column from bottom to top at an ascending rate of about 9 m/h and exits via an overflow located at the top of the release zone. The two 2-ethylhexanol flows enable a temperature gradient, which is necessary to control the gelling and dehydration kinetics of the sol, to be obtained in the column.

The 2-ethylhexanol leaving the column is passed to the reservoir 5 through the line 54. In a device which is not shown in FIG. 1, it is pre-purified by washing with water and distillation in order to remove the dissolved ammonium sulphate, the organic residues (urea, hexamethylenetetramine and formol) and the water extracted from the sol.

At the lower end of the column, the microspheres are collected in the receiving tank 4 containing 1N ammonia homogenized and kept at 40° C. by means of the closed circuit 41.

The production is about 100 g/h per injector, but may be increased by using several injectors.

The microspheres are washed thoroughly with dilute ammonia (0.1N) and then with water and dried at 120° C. They are then calcined at 420° C. under a nitrogen atmosphere for 4 hours.

The catalyst A thus obtained has the following characteristics:

Ni/Cr atomic ratio=0.34
diameter of the microspheres=0.5 to 2.5 mm
apparent density=1.25 g/cm$^3$
specific surface area (BET)=185 m$^2$/g
pore volume=0.05 cm$^3$/g
bulk crush strength (BCS)=2.1 kg/cm$^2$

EXAMPLE 2

Catalyst B

The procedure is as in Example 1, except that the ammonia solution in the receiving tank for the microspheres has a concentration of 11N instead of 1N.

The characteristics of the catalyst B thus obtained are as follows:

Ni/Cr atomic ratio=0.27
diameter of the microspheres=0.5 to 2.5 mm
apparent density=1.4 g/cm$^3$
specific surface area (BET)=102 m$^2$/g
pore volume=0.07 cm$^3$/g
bulk crush strength (BCS)=7.5 kg/cm$^2$

EXAMPLE 3

Catalyst C

The procedure is as in Example 1, but without addition of silica sol; a catalyst C having the following characteristics is obtained:

Ni/Cr atomic ratio=0.25
diameter of the microspheres=0.5 to 2.5 mm
apparent density=1.5 g/cm$^3$
specific surface area (BET)=25 m$^2$/g
pore volume=0.09 cm$^3$/g

EXAMPLE 4

Catalyst D

The procedure is as in Example 1, reducing the nickel content, that is to say using an aqueous solution prepared by dissolving 550 g of basic chromium sulphate and 45 g of nickel chloride hexahydrate in 440 g of water as the starting material.

The catalyst D thus obtained has the following characteristics:

Ni/Cr atomic ratio=0.07
diameter of the microspheres=0.5 to 2.5 mm
apparent density=1.38 g/cm$^3$
specific surface area (BET)=187 m$^2$/g
pore volume=0.044 cm$^3$/g

EXAMPLE 5

Catalyst E

The procedure is as in Example 1, except that the microspheres are calcined at 350° C. instead of 420° C.

The catalyst E thus obtained has the following characteristics:

Ni/Cr atomic ratio=0.37
diameter of the microspheres=0.5 to 2.5 mm
apparent density=1.1 g/cm$^3$
specific surface area (BET)=178 m$^2$/g
pore volume=0.09 cm$^3$/g

EXAMPLE 6

Catalyst F (Comparative)

The procedure is as in Example 1, omitting the nickel. The starting aqueous solution consists solely of basic chromium sulphate (550 g) and water (475 g).

The characteristics of this catalyst F, prepared for comparison, are as follows:

diameter of the microspheres=0.5 to 2.5 mm
apparent density=1.04 g/cm$^3$ specific surface area (BET)=209 m³/g
pore volume=0.052 cm³/g
bulk crush strength (BCS)=3.8 kg/cm²

Figure 2:
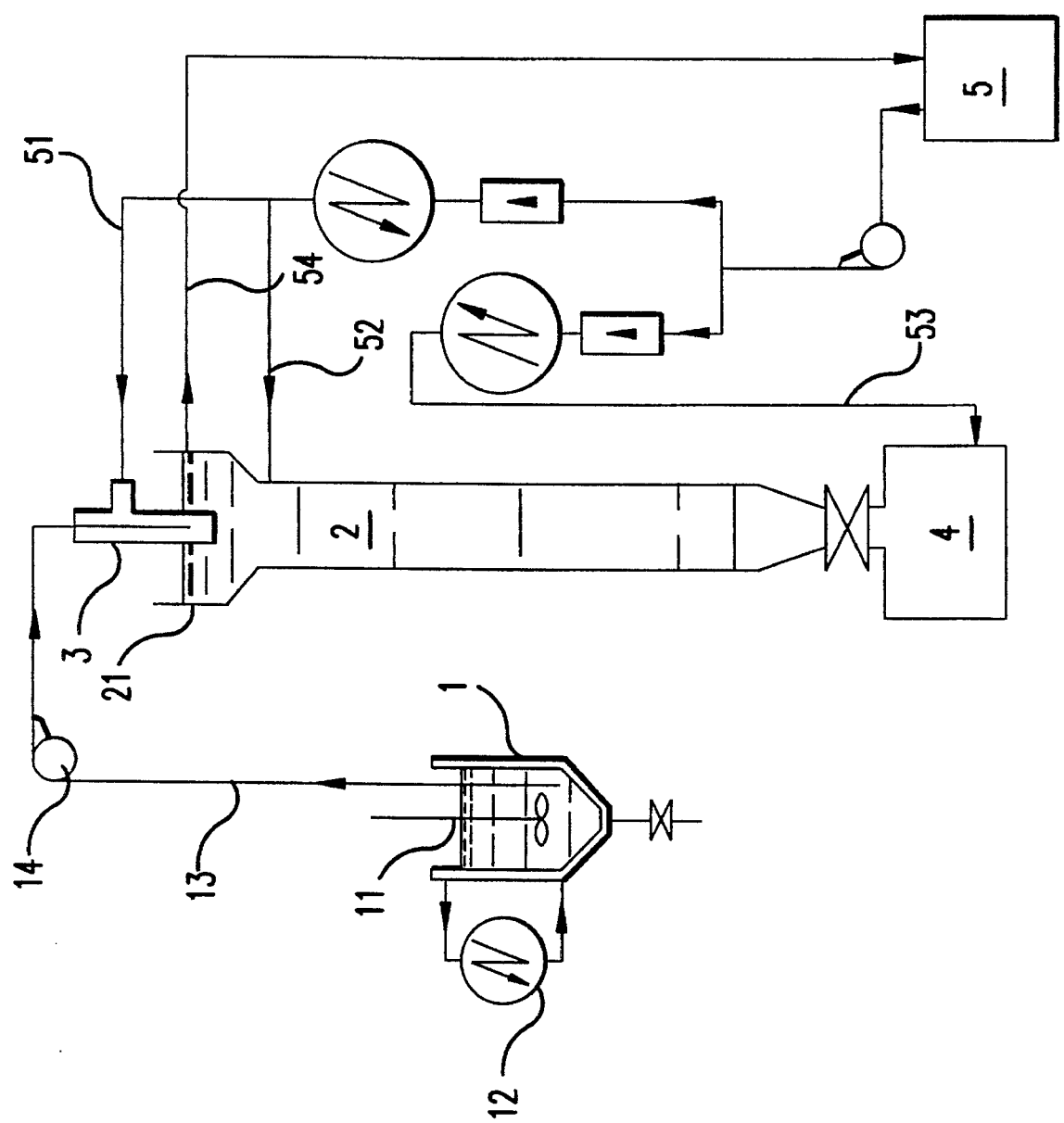

If the ammonia contained in the receiving tank is replaced by 2-ethylhexanol at 120° C. by modifying the apparatus in accordance with appended FIG. 2, a product is obtained which has the following characteristics:
apparent density: 1.07 g/cm³
specific surface area: 203 m²/g
bulk crush strength (BCS): 2.3 kg/cm²

EXAMPLE 7

Catalyst G (Comparative)

The procedure is as in Example 6 except that the microspheres are calcined at 350° C. instead of 420° C.

The catalyst thus obtained has the following characteristics:
diameter of the microspheres=0.5 to 2.5 mm
apparent density=1.3 g/cm³
specific surface area (BET)=181 m²/g
pore volume=0.05 cm³/g

EXAMPLE 8

Catalyst H (Comparative)

The procedure is as in Example 1 without the addition of either nickel or silica sol. The starting aqueous solution consists solely of basic chromium sulphate (550 g) and water (475 g).

The characteristics of this catalyst H, prepared for comparison, are as follows:
diameter of the microspheres=0.5 to 2.5 mm
apparent density=1.4 g/cm²
specific surface area (BET)=10 m²/g
pore volume=0.28 cm³/g

EXAMPLE 9

Catalyst I

A solution of 200 g of chromium nitrate nonahydrate and 118.8 g of nickel chloride hexahydrate in 1000 g of water is prepared and heated at 80° C. for 2 hours. After cooling to 20° C., this solution is then gelled by adding 190 ml of 14.7N aqueous ammonia.

The gel obtained is then washed twice with 450 ml of 0.1N aqueous ammonia, then twice with 450 ml of distilled water, each washing step being followed by a filtration.

The powder obtained is then dried for 14 hours at 100° C. under vacuum (20 kPa) and then calcined at 350° C. under a nitrogen atmosphere for 4 hours.

The characteristics of the catalyst I thus obtained are as follows:
specific surface area (BET)=160 m²/g
pore volume=0.74 cm³/g

EXAMPLE 10

Catalyst J (Comparative)

The procedure is as in Example 9 except that the solution of chromium and nickel salts is heated at 40° C. instead of 80° C.

The catalyst J thus obtained has the following characteristics:
specific surface area (BET)=139 m²/g
pore volume=0.60 cm³/g

EXAMPLE 11

Catalyst K

An aqueous chromium and nickel solution is prepared by dissolving 274 g of nickel chloride hexahydrate in 200 g of water and then by adding 275 g of basic chromium sulphate and 183.5 g of water.

112 g of CECASOL are added to this solution and 390 ml of an 11N ammonia solution are then added until the sol sets completely. The gel obtained is washed with a dilute ammonia solution and with water before being dried at 120° C. for 15 hours and calcined at 250° C. for 4 hours.

A 12% aqueous polyvinyl alcohol solution is added to the powder collected and the mixture is then dried at 85° C. for 15 hours. The mixture is then shaped by pelleting and calcined at 420° C. for 4 hours.

The catalyst K thus obtained has the following characteristics:
Cr=24.7% by mass
Ni=20.15% by mass
Ni/Cr atomic ratio=0.42
specific surface area (BET)=54.8 m²/g
pore volume=0.162 cm³/g

EXAMPLE 12

Catalyst L (Comparative)

A chromium and nickel solution is prepared by mixing at room temperature 80 ml of a 1M $Cr(NO_3)_3 \cdot 9H_2O$ solution and 80 ml of a 1M $NiCl_2 \cdot 6H_2O$ solution. The mixture is then neutralized with 50 ml of 14N ammonia and the product, recovered by centrifuging, is dried at 100° C. for 15 hours.

0.4 g of graphite and 5.1 g of a 12% aqueous polyvinyl alcohol solution are added to the powder obtained and the mixture is then dried at 100° C. (15 hours) and shaped into pellets. The final product is calcined at 350° C. for 4 hours.

The catalyst L thus obtained has the following characteristics:
Ni/Cr atomic ratio=0.95
specific surface area (BET)=82.8 m²/g
pore volume=0.17 cm³/g

FLUORINATION EXAMPLES

In the following examples:
the percentages indicated are molar percentages;
the hydrofluoric acid used is a commercial product containing only traces of water;
the starting 1-chloro-2,2,2-trifluoroethane (F133a) is a 99.9% pure product;

the reactor used is a 250 ml Inconel tube heated by means of a fluidized bath of alumina.

The activation of the catalyst by means of HF is carried out in this reactor on a 100 ml sample. After drying for 3 hours under nitrogen (5 l/h) at 250° C., hydrofluoric acid is added progressively, at the same temperature, to nitrogen for a period of 5 hours (2 mols of HF introduced in the course of five hours). After passing through exothermicity peaks, the HF flow rate is increased in order to reach 1 mol/h and the temperature is then brought to 350° C. A temperature plateau is observed under these conditions for 8 hours.

Before they are introduced into the reactor, the reagents are mixed and heated to the reaction temperature in an Inconel preheater.

After washing with water—in order to remove the hydracids—and drying over $CaCl_2$, the reaction products are analyzed on-line by gas phase chromatography.

EXAMPLES 13 TO 15

F133a fluorination tests are carried out under atmospheric pressure, in the absence of oxygen, using catalysts A, D and F, activated by the procedure described above. The fluorination results are summarized in Table 1.

It is found that the activity of catalyst F (chromium on its own) falls much more rapidly than that of catalysts A and D (nickel/chromium) and that the selectivities are also less good.

TABLE 1

| CATALYST | A Example 13 | | D Example 14 | | F comparative Example 15 | |
|---|---|---|---|---|---|---|
| Age of the catalyst (hours) | 26 | 221 | 22 | 220 | 24 | 221 |
| HF/F133a molar ratio | 4.1 | 4.2 | 3.8 | 3.9 | 4.0 | 4.0 |
| Contact time (s) | 3.9 | 3.8 | 4.1 | 4.0 | 3.9 | 3.9 |
| Temp. (°C.) | 350 | 350 | 350 | 350 | 350 | 350 |
| Degree of conversion of F133a (%) | 22.4 | 22.6 | 20.2 | 18.2 | 19.5 | 9.1 |
| Selectivity for 134a ($CF_3CH_2F$) (%) | 97.3 | 97.3 | 97.9 | 98.3 | 96.9 | 94.5 |
| Selectivity for F1122 ($CF_2=CHCl$) (%) | 1.3 | 1.3 | 1.0 | 1.1 | 1.5 | 3.3 |
| Selectivity for F123 ($CF_3CHCl_2$) (%) | 0 | 0 | 0 | 0 | 0.3 | 1.1 |
| Selectivity for F124 ($CF_3CHClF$) (%) | 0.3 | 0.3 | 0.2 | 0.3 | 0.5 | 0.5 |
| Selectivity for F125 ($CF_3CHF_2$) (%) | 0.1 | 0 | 0 | 0 | 0 | 0 |
| Selectivity for F143a ($CF_3CH_3$) (%) | 0.3 | 0.3 | 0.2 | 0.3 | 0.3 | 0 |

EXAMPLES 16 AND 17

F133a fluorination tests are carried out under an absolute pressure of 1.5 MPa in the presence of oxygen by injection of air and with catalysts E and G activated in accordance with the procedure described above. The fluorination results are summarized in Table 2.

TABLE 2

| CATALYST | E Example 16 | | G comparative Example 17 | |
|---|---|---|---|---|
| Age of the catalyst (hrs.) | 22 | 268 | 22 | 265 |
| HF/F113a molar ratio | 5.1 | 5.1 | 5.1 | 5.1 |
| $O_2$/F133a molar ratio | 0.01 | 0.01 | 0.01 | 0.02 |
| Contact time (s) | 19.6 | 19.6 | 19.6 | 19.7 |
| Temperature (°C.) | 350 | 350 | 350 | 350 |
| Degree of conversion of F133a (%) | 23.2 | 24.7 | 21.6 | 19.7 |
| Selectivity for F134a (%) | 96.5 | 95.9 | 93.3 | 89.8 |
| Selectivity for F1122 (%) | 0.05 | 0.04 | 0.1 | 0.1 |
| Selectivity for F123 (%) | 0.5 | 0.4 | 2.1 | 3 |
| Selectivity for F124 (%) | 0.5 | 0.9 | 1.1 | 1.3 |
| Selectivity for F125 (%) | 0.2 | 0.4 | 0.3 | 0.2 |
| Selectivity for F143a (%) | 0 | 0.02 | 0.1 | 0.1 |

Entirely as before, catalyst E (Ni/Cr) (Example 16) gives rise to a more stable activity and to a better selectivity than catalyst G without nickel (Example 17).

EXAMPLES 18, 19 AND 20

These examples, which are summarized in Table 3 below, were carried out using catalysts C and H without silica and permit comparison of the results of F133a fluorination under atmospheric pressure in the absence of oxygen.

After 548 hours in use, catalyst C of Example 19 was subjected to regeneration by treatment under air (1 mol/hour) at 300° C. for 24 hours. Catalyst C regenerated in this way was then used for the tests of Example 20.

Examination of the results enables the effect of nickel on the activity of the catalyst, despite the absence of silica, to be estimated.

It is also found that the regenerated catalyst C (Example 20) has an activity comparable to that of catalyst C at the start of the test.

TABLE 3

| CATALYST | H comparative Example 18 | C Example 19 | | | Regenerated C Example 20 | |
| --- | --- | --- | --- | --- | --- | --- |
| Age of the catalyst (hrs.) | 47 | 65 | 338 | 548 | 48(*) | 245(*) |
| HF/F133a molar ratio | 3.9 | 4 | 4 | 4 | 4 | 4 |
| Contact time (s) | 4 | 4.1 | 4.1 | 4.2 | 4.8 | 4.6 |
| Temperature (°C.) | 350 | 350 | 350 | 350 | 350 | 350 |
| Degree of conversion of F133a (%) | 4 | 20.4 | 18.6 | 14.8 | 20.4 | 20.8 |
| Selectivity for F134a (%) | 87.5 | 97.1 | 97.3 | 98 | 98.5 | 98.1 |
| Selectivity for F1122 (%) | 5 | 1 | 1.1 | 1.4 | 1 | 1 |
| selectivity for F123 (%) | 2.5 | 0.5 | 0.3 | 0.3 | 0 | 0 |
| Selectivity for F124 (%) | 1.3 | 0.5 | 0.3 | 0.3 | 0.2 | 0.2 |
| Selectivity for F125 (%) | 0 | 0 | 0 | 0 | 0 | 0 |
| Selectivity for F143a (%) | 1.3 | 0 | 0 | 0 | 0 | 0 |

(*)after regeneration

EXAMPLE 21

This example, summarized in Table 4 below, was carried out at atmospheric pressure in the absence of oxygen, using the catalysts I and J prepared from sols heated at 80° and 40° C. respectively.

TABLE 4

| CATALYST | I | J (comparative) |
| --- | --- | --- |
| Age of the catalyst (hrs.) | 28 | 21 |
| HF/133a molar ratio | 4.4 | 4.3 |
| Contact time (s) | 3.8 | 3.9 |
| Temperature (°C.) | 350 | 350 |
| Degree of conversion of F133a (%) | 21.2 | 16.3 |
| Selectivity for F134a (%) | 98.3 | 97.5 |
| Selectivity for F1122 (%) | 0.9 | 1.5 |
| Selectivity for F123 (%) | 0 | 0.1 |
| Selectivity for F124 (%) | 0.2 | 0.2 |
| Selectivity for F125 (%) | 0.2 | 0.1 |
| Selectivity for F143a (%) | 0.3 | 0.6 |

Examination of the results enables the effect of the temperature of preparation of the sol of chromium and nickel on the activity of the catalyst, to be estimated.

Although the invention has been described in conjunction with specific embodiments, it is evident that many alternatives and variations will be apparent to those skilled in he art in light of the foregoing description. Accordingly, the invention is intended to embrace all of the alternatives and variations that fall within the spirit and scope of the appended claims. The above references are hereby incorporated by reference.

We claim:

1. A catalyst based on chromium and nickel oxides resistant to crystallization and selective in gas phase fluorination reactions by partial inhibition of oxidation of hydrochloric acid in the presence of chromium, comprising a Ni/Cr atomic ratio between 0.05 and 5 and said catalyst is obtained by a process consisting essentially of:
   a) forming sol of chromium (III) and nickel (II) hydroxides,
   b) gelling said sol, and
   c) drying and calcining the gelled sol to a temperature between 250° and 450° C.

2. Catalyst according to claim 1, wherein the Ni/Cr atomic ratio is between 0.1 and 3.5.

3. Catalyst according to claim 1, wherein the sol of chromium and nickel hydroxides is obtained from chromium(III) sulphate, acetate or nitrate and from nickel chloride, nitrate or sulphate.

4. Catalyst according to claim 1, wherein the sol also contains at least one additive selected from:
   crystalline $Cr_2O_3$ powder
   alumina monohydrate
   hexamethylenetetramine and/or urea
   colloidal silica
   wetting agents
   thickeners.

5. Catalyst according to claim 1, wherein the formation of the sol comprises a heating step at a temperature of between 60° and 100° C.

6. Catalyst according to claim 1, wherein the sol is formed in the presence of a complexing agent for chromium and/or nickel.

7. Catalyst according to claim 1, wherein the sol is gelled by means of aqueous ammonia.

8. Catalyst according to claim 1 in the form of microspheres, wherein the gelling of the sol of chromium and nickel hydroxides is obtained by a process further consisting essentially of:
   (a) dispersing the sol in the form of droplets in an organic solvent which is immiscible or sparingly miscible with water, and gelling at elevated temperature;
   (b) collecting the microspheres formed in the same organic solvent or in an ammonia solution;
   (c) washing the microspheres with dilute ammonia and then with water.

9. A catalyst based on chromium and nickel oxides resistant to crystallization and selective in gas phase fluorination reactions by partial inhibition of oxidation of hydrochloric acid in the presence of chromium, comprising a Ni/Cr atomic ratio between 0.05 and 5 and said catalyst is obtained by a process consisting essentially of:
   (a) forming a sol of chromium (III) and nickel (II) hydroxides,
   (b) dispersing the sol in the form of droplets in an organic solvent of butanol, hexanol, 2-ethylpentanol or 2-ethylhexanol,
   (c) gelling the sol at elevated temperatures,
   (d) collecting the microspheres formed in the same organic solvent or in an ammonia solution,
   (e) washing the microspheres with dilute ammonia and then with water, and
   (f) drying and calcining the gelled sol to a temperature between 250° and 450° C.

10. Catalyst according to claim 1, wherein said catalyst is in the form of pellets or extruded products.

11. Catalyst according to claim 1, wherein the calcination is carried out at a temperature of between 300° and 420° C.

12. Process for fluorination of at least one saturated or olefinic halogenated hydrocarbon, said process comprising contacting said halogenated hydrocarbon with HF in the gas phase in the presence of the catalyst according to claim 1.

13. Process according to claim 12, wherein the halogenated hydrocarbon is 1-chloro-2,2,2-trifluoroethane.

14. Catalyst according to claim 2, wherein the Ni/Cr atomic ratio is between 0.15 and 3.

15. Catalyst according to claim 5, wherein the heating step temperature is between 80° and 95° C.

16. A catalyst based on chromium and nickel oxides resistant to crystallization and selective in gas phase fluorination reactions by partial inhibition of oxidation of hydrochloric acid in the presence of chromium, comprising a Ni/Cr atomic ratio between 0.05 and 5 and said catalyst is obtained by a process consisting essentially of:

(a) forming a sol of chromium (III) and nickel (II) hydroxides;

(b) dispersing the sol in the form of droplets in an organic solvent of 2-ethylhexanol;

(c) gelling the sol at elevated temperatures;

(d) collecting the microspheres formed in the same organic solvent or in an ammonia solution;

(e) washing the micro spheres with dilute ammonia and then with water; and (f) calcining the gelled sol to a temperature between 250° and 450° C.

17. The catalyst of claim 16, wherein step (e) includes a step of optionally drying the microspheres at a temperature between 80° and 200° C.

* * * * *

UNITED STATES PATENT AND TRADEMARK OFFICE
CERTIFICATE OF CORRECTION

PATENT NO. : 5,523,500
DATED      : June 4, 1996
INVENTOR(S) : CHEMINAL, et al.

It is certified that error appears in the above-indentified patent and that said Letters Patent is hereby corrected as shown below:

Title page,
Item [63] delete "968,394" and insert --986,394--.

Signed and Sealed this

Seventeenth Day of December, 1996

Attest:

BRUCE LEHMAN

Attesting Officer

Commissioner of Patents and Trademarks